US00PP14797P3

(12) United States Plant Patent
Hasegawa

(10) Patent No.: US PP14,797 P3
(45) Date of Patent: May 18, 2004

(54) HYBRID CARNATION PLANT NAMED 'CFPC TIARA'

(50) Latin Name: *Dianthus caryophyllus*
Varietal Denomination: CFPC Tiara

(75) Inventor: Oscar T. Hasegawa, Salinas, CA (US)

(73) Assignee: California Florida Plant Company, L.P., Salinas, CA (US)

( * ) Notice: Subject to any disclaimer, the term of this patent is extended or adjusted under 35 U.S.C. 154(b) by 0 days.

(21) Appl. No.: 10/208,116

(22) Filed: Jul. 29, 2002

(65) Prior Publication Data

US 2004/0019944 P1 Jan. 29, 2004

(51) Int. Cl.[7] ..... A01H 5/00
(52) U.S. Cl. ..... Plt./278
(58) Field of Search ..... Plt./278

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of carnation plant producing attractive bright red flowers.

1 Drawing Sheet

Classification: The present invention relates to a new Hybrid *Dianthus caryophyllus* plant.

Variety denomination: The new plant has the varietal denomination 'CFPC Tiara'.

BACKGROUND OF THE INVENTION

The present invention relates to a new and distinct variety of carnation plant which is a cross of 'CFPC Selena' (U.S. Plant Pat. No. 11,899) as a seed parent and an undistributed, unpatented seedling identified as '970110'. The varietal denomination of the new variety is 'CFPC Tiara'.

SUMMARY OF THE INVENTION

Among the novel characteristics possessed by the new variety which distinguish it from other varieties of which I am aware, are its attractive bright red flowers which retain color without fading. When grown in a greenhouse in Salinas, Calif., in 4½ inch plastic pots, pinched plants are about 7 inches tall and about 7 inches in diameter. Flower diameter averages about 2⅛ inches with a crown of about 1 inch (average). Foliage is about 4 inches long and about ½ inch wide at its widest point.

Asexual reproduction by propagation by cuttings of the new variety as performed in Salinas, Calif., shows that the foregoing and other distinguishing characteristics come true to form and are established and transmitted through succeeding propagation.

COMPARISON WITH PARENTS

The new variety differs from its parents in flower color. 'CFPC Selena' produces crimson mauve flowers and the male parent produced dark red flowers. The new variety produces flowers which are a non-fading red color.

BRIEF DESCRIPTION OF ILLUSTRATION

The accompanying illustration shows a typical specimen of the vegetative growth and flowers of the new variety depicted in color as nearly true as it is reasonably possible to make the same in color illustration of this character.

DESCRIPTION OF THE NEW VARIETY

The following is a detailed description of the new variety, with color terminology in accordance with The Royal Horticultural Society Colour Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of 110-day-old plants grown inside commercial greenhouses at Salinas, Calif. The height of plant and flower and foliage size are established as an average using standard commercial cultural practices.

Classification:
- *Botanical.*—Hybrid *Dianthus caryophyllus.*
- *Commercial.*—Carnation, standard disbud, type, suitable for cut flower production and as a pot spray.

Plant:
- *Height.*—About 7 inches.
- *Form.*—Herbaceous.
- *Growing habit.*—Semi-upright.
- *Blooming habit.*—As a spray (pot).
- *Blooming season.*—Year round.
- *Rooting time/habit.*—About 18 days.
- *Breaking action.*—Very vigorous and free-breaking plant habit with strong straight stems.
- *Mutation prone.*—No.
- *Diseases resistance.*—Good, resistance to soil-borne diseases such as Fusarium oxysporum, and F. graminearum and root-rots such as damping off, water molds and the like as is typical of carnations.
- *Temperature tolerance.*—Wide range.

Foliage (base of plant):
- *Color.*—Upper side: Near 137A. Lower side: Near 137B.
- *Size.*—About 4 inches long and about ½ inch wide.
- *Leaf base and apex.*—Leaf base edge smooth, color near 145D; leaf apex edge smooth, color near 137A.
- *Quantity.*—Numerous.
- *Shape.*—Lanceolate.

*Texture.*—Smooth.
*Ribs.*—Central keel.
*Arrangement.*—Bi-lateral along stem.
*Stem.*—Color: Near 137D. Size: Stem diameter about 3/16 inch.
*Bud.*—Shape: Ovoid. Color: Near 134A. Length: About 1 inch. Diameter: About 7/16 inch.
*Calyx.*—Sepals: About 5. Length: About 3/8 inch. Width: About 3/8 inch. Color Outside: Near 143C. Inside: Near 147D.

Bloom:
*Shape.*—Rounded.
*Size.*—Diameter: About 2 inches. Depth: About 1 inch.
*Borne.*—As a spray.
*Color.*—General tonality: Red. Upper side: Near 46B. Lower side: Near 47A. Center: Near 46B. Outer petals: Near 46B.
*Permanence.*—Dry up on receptacle.
*Keeping quality.*—Very good.
*Fragrance.*—Slight.

Petalage:
*Quantity.*—About 35.
*Outer petal size.*—Length: About 1 7/8 inches. Width: About 1 5/16 inches.
*Central petal size.*—Length: About 1 5/8 inches. Width: About 9/16 inch.
*Texture.*—Smooth.
*Appearance.*—Shiny, petal edge very finely serrated, color near 46B.
*Form.*—Fan shaped.

Reproductive organs:
*Stamen.*—None.
*Anthers.*—None.
*Filaments.*—None.
*Pistil.*—1. Length: About 1 1/16 inches. Color: Whiter than 155D.
*Stigma.*—2 or 3. Color: Near 55D.
*Fertility.*—Male: Sterile. Female: Good.
*Ovary.*—Shape: Conical. Color Base: Near 155D. Body: Near 144B. Apex: Near 144B.
*Fruit.*—No fruit or seed produced.

I claim:

1. A new and distinct carnation plant of the variety substantially as herein shown and described.

* * * * *

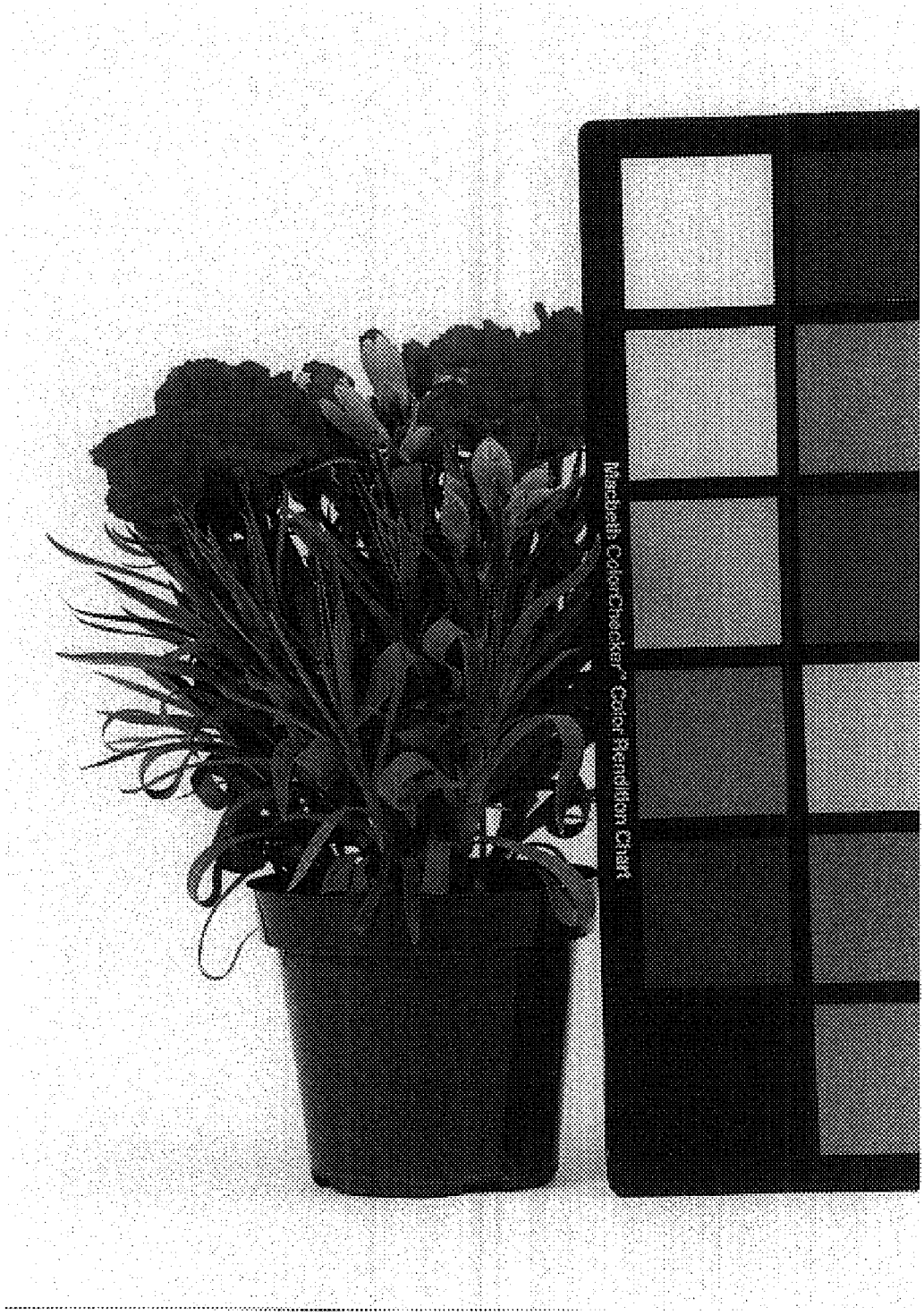
Macbeth ColorChecker® Color Rendition Chart